United States Patent [19]
Olive et al.

[11] Patent Number: 5,855,594
[45] Date of Patent: Jan. 5, 1999

[54] SELF-CALIBRATION SYSTEM FOR CAPTURE VERIFICATION IN PACING DEVICES

[75] Inventors: Arthur L. Olive, Stacy; Brian D. Pederson, Woodbury; Veerichetty A. Kadhiresan, Little Canada; Donald L. Villalta, Minneapolis, all of Minn.

[73] Assignee: Cardiac Pacemakers, Inc., St. Paul, Minn.

[21] Appl. No.: 907,609

[22] Filed: Aug. 8, 1997

[51] Int. Cl.⁶ ............................. A61N 1/362; A61N 1/36
[52] U.S. Cl. .................................. 607/28; 607/11; 607/27
[58] Field of Search .................................. 607/27, 28, 11

[56] References Cited

U.S. PATENT DOCUMENTS

| | | |
|---|---|---|
| 5,036,849 | 8/1991 | Hauck et al. . |
| 5,172,690 | 12/1992 | Nappholz et al. . |
| 5,176,138 | 1/1993 | Thacker . |
| 5,222,493 | 6/1993 | Sholder . |
| 5,284,136 | 2/1994 | Hauck et al. . |
| 5,318,597 | 6/1994 | Hauck et al. . |
| 5,320,643 | 6/1994 | Roline et al. . |
| 5,324,310 | 6/1994 | Greeninger et al. . |
| 5,330,512 | 7/1994 | Hauck et al. . |
| 5,336,244 | 8/1994 | Weijand . |
| 5,350,410 | 9/1994 | Kleks et al. . |
| 5,411,533 | 5/1995 | Dubreuil et al. . |
| 5,443,485 | 8/1995 | Housworth et al. . |
| 5,713,933 | 2/1998 | Condle et al. . |
| 5,718,720 | 2/1998 | Prutchi et al. . |

*Primary Examiner*—William E. Kamm
*Assistant Examiner*—Carl H. Layno
*Attorney, Agent, or Firm*—Haugen and Nikolai, P.A.

[57] ABSTRACT

A cardiac pacing and sensing system includes a body implantable unit for generating tissue stimulation pulses and manipulating information based on sensed signals, and a catheter for transmitting pulses from the unit to a pacing electrode adjacent myocardial tissue. The unit incorporates circuitry for generating response values, one associated with each stimulation pulse, based on a predetermined characteristic or parameter of the signals evoked by the pulses. To evaluate the efficacy of the parameter in distinguishing capture versus non-capture, the stimulation pulses are generated according to a protocol of high energy pulses guaranteed to effect capture interspersed with low energy pulses guaranteed not to effect capture. Data, accumulated and sorted into separate "capture" and "non-capture" sets, provides respective capture and non-capture composite values. The ratio of the composite values is compared to a predetermined threshold, to generate an indication either accepting or rejecting the chosen parameter. A parameter, once accepted, can be employed in a self-test that either increments or decrements stimulation of signals to evaluate the capture threshold. Optionally, two or more designated parameters can be screened simultaneously and compared, with the most favorable ratio then being compared to the threshold.

34 Claims, 9 Drawing Sheets

SELF-CALIBRATION SYSTEM FOR CAPTURE VERIFICATION IN PACING DEVICES

BACKGROUND OF THE INVENTION

The present invention relates to cardiac pacers and other tissue stimulating devices, and more particularly to the calibration and testing of such devices to improve recognition of a desired result such as capture and to minimize the stimulation energy required to achieve the desired result.

Cardiac pacing devices are implanted in the body to deliver electrical stimulation pulses from a pulse generator to myocardial tissue, usually at the ventricle or the atrium. The function of each pulse is to cause a depolarization of the myocardial tissue at and near the point of pulse delivery, resulting in a ventricular or atrial contraction, i.e. a heart beat. This result is frequently referred to as "capture".

The energy of the stimulation pulse is a function of pulse amplitude and pulse duration. While the primary requirement of each stimulation pulse is an energy level sufficient to achieve capture, it also is advantageous to avoid excessive energy levels, to increase the life of the pulse generator battery. Thus, the goal is to stimulate the tissue with pulses near the minimum requirement for capture, i.e. the capture threshold, while providing a margin for safety.

The difficulty in achieving this goal arises in large part due to variations in the stimulation threshold. Not only does the threshold vary over different patients, it also may vary with time in each patient. More particularly, low thresholds are observed immediately after implant. Tissue inflammation at and near the stimulation electrode considerably increases the threshold during the first several weeks after implant. Over the longer term, reduction in the inflammation lowers the threshold, although the chronic threshold remains above the initial level at implant. Changes in an individual's activity, e.g. vigorous exercise, can cause short term changes in the stimulation threshold. Stimulation thresholds can be influenced by drugs such as catecholamines, beta-blockers, cardiosteriods and antiarrhythmic drugs.

The prior art includes examples of devices intended to change tissue stimulation levels to accommodate changes in stimulation thresholds. These devices typically incorporate an autocapture feature, e.g. a controlled varying of stimulation pulse levels in combination with a sensing of the cardiac response. In ventricle pacing, depolarization of the ventricle evokes an R wave (also known as a QRS complex) which can be sensed and processed to verify depolarization. Sensing circuitry can be incorporated into the pacing device. For example, see U.S. Pat. No. 5,330,512 (Hauck, et al). Other parameters can be sensed to confirm adequate stimulation levels, including oxygen concentration in the blood as in U.S. Pat. No. 5,176,138 (Thacker), and changes in fluid pressure in the heart as in U.S. Pat. No. 5,320,643 (Roline).

In comparing the above techniques, R wave sensing has the best potential for unambiguously indicating the presence or absence of an evoked response, i.e. capture verification. However, when the pacing device is used to sense the evoked response, lead polarization from the tissue stimulating pulse diminishes the ability to sense an evoked response and also can cause a false positive indication of capture. One attempt to address this problem is disclosed in U.S. Pat. No. 5,350,410 (Kleks, et al). Kleks teaches generating two stimulation pulses separated by a time less than the natural refractory period. The sensed response to the first pulse is assumed to include an evoked response and a lead polarization signal, while the second sensed response is assumed to include only the lead polarization Pulses at several levels are tested with several detection sensitivity levels to provide "polarization templates". To be judged an evoked response, a given signal must vary sufficiently from the polarization template. This approach, while perhaps diminishing the negative impact of lead polarization, does not address the variations in R waves and other evoked signals among different patients and over time in connection with a given individual. It also does not address the risk that the reliability of a previously designated response signal parameter may diminish, due to interference from physiological or extrinsic noise, or due to a physiological change.

Therefore, it is an object of the present invention to provide a process to verify capture or another desired response, that involves assessing the reliability of a chosen parameter of an evoked signal as a reliable indication of the response.

Another object is to provide a system, operable with a device that delivers stimulation pulses and senses evoked signals, for accumulating multiple measurements of a sensed signal characteristic to more reliably assess the utility of that characteristic in confirming capture.

A further object is to provide a device capable of sensing two or more characteristics of evoked signals and comparing the characteristics as to their efficacy in confirming capture or another desired result.

Another object is to provide a system which, at predetermined intervals, automatically and adaptively generates measurements used to demarcate signals or calculated parameters associated with capture and non-capture, respectively.

Yet another object is to provide a system and process associated with an implanted pacer or other stimulation device, for more effectively adjusting the level of stimulation pulses to track changes in a patient's stimulation threshold.

SUMMARY OF THE INVENTION

To achieve these and other objects, there is provided a process for testing the efficacy of a sensed parameter as an indication of tissue stimulation. The process proceeds according to the following steps:

a. applying a plurality of first pulses to tissue, each of the first pulses having at least a first level of intensity known to evoke a desired response in the tissue;

b. applying a plurality of second pulses to the tissue in a manner that intersperses the second pulses within the plurality of first pulses, each of the second pulses having at most a second level of intensity known to be insufficient to evoke the desired response, wherein each of the pulses is temporally distinguishable from the other pulses;

c. after applying each of the pulses, sensing the tissue to provide a response value based on a predetermined parameter, each one of the response values corresponding to one of the first and second pulses;

d. accumulating and sorting the response values into a first set of the response values corresponding to the first pulses, and a second set of the response values corresponding to the second pulses;

e. combining the response values of the first and second sets into respective first and second composite values;

f. comparing the first composite value to the second composite value, to produce a difference factor based on the comparison; and g. comparing the difference factor to a predetermined threshold and alternatively:
  (i) indicating an acceptance of the parameter responsive to determining that the difference factor is at least equal to the threshold; and
  (ii) indicating a rejection of the parameter responsive to determining that the difference factor is less than the threshold.

A salient feature of this approach is that the chosen parameter can be evaluated as to its reliability in terms of unambiguously distinguishing capture from non-capture. The chosen parameter can be a peak-to-peak amplitude, a signal voltage level, or a voltage level of an integration or differentiation of the signal. Multiple measurements, preferably 50 or more, are combined to provide mean and standard deviation information. In this manner, two signatures are developed, corresponding respectively to capture and non-capture pacing.

The two signatures must exhibit a recognition differential sufficient to distinguish between capture and non-capture. This may be expressed as a signal-to-noise ratio (SNR) obtained by dividing the capture level by the non-capture level. For example, if the threshold is five, the parameter is accepted if the difference factor, i.e. the SNR, is at least equal to five and rejected if the difference factor is less than five.

When a given parameter is accepted, the process further can involve testing for the capture threshold, e.g. by incrementally reducing the energy level (amplitude, pulse width or both) from a given level known to evoke capture. Thus a minimum stimulation pulse level necessary to achieve capture is determined and enhanced by a safety factor as deemed appropriate.

The pulses are advantageously interspersed in a manner that avoids the occurrence of two or more consecutive second pulses. Even more preferably, the pulse generator is controlled to provide alternating first and second pulses. The pulses are preferably generated at a frequency that exceeds an intrinsic heart rate. The result is a sequence of sensed response signals consistent with the pattern of alternating capture and non-capture. The signatures of capture and non-capture are obtained by accumulating the sensed information and sorting the data into two sets consistent with the pattern of alternating stimulation signals.

Further in accordance with the present invention, there is provided a self-testing system for determining the efficacy of a detected response in tissue as an indication of stimulation. The system includes a pulse generator and a conductive pathway coupled between the pulse generator and tissue, for delivering pulses to the tissue. A control means, operatively coupled to the pulse generator, selectively varies the intensity of the pulses. This causes the pulse generator to deliver the pulses according to a protocol in which: (i) several first pulses having a first level of intensity known to achieve capture are interspersed among several second pulses having at most a second level of intensity known as insufficient to achieve capture; and (ii) each of the pulses is temporally distinct from the others.

A detecting means senses a response signal in the tissue following each of the first and second pulses, and is adapted for generating at least a first response value associated with each response signal based on a first characteristic of the response signal. A storage means is adapted for accumulating the response values, and a sorting means is provided for sorting the accumulated response values into a first set corresponding to the first pulses and second set corresponding to the second pulses. A first processing means combines the response values to generate first and second composite values based on the first and second sets, respectively. A second processing means, operatively coupled to the first processing means, compares the first and second composite values and generates a difference factor based on the degree of difference between the first and second composite values. A third processing means, coupled to receive the output of the second processing means, is adapted to compare the difference factor to a predetermined threshold and further is adapted to provide, alternatively: (i) an indication of acceptance of the characteristic, responsive to determining that the difference factor is at least as great as the threshold; and (ii) an indication of rejection of the characteristic, responsive to determining that the difference factor is less than the threshold.

In one advantageous approach, the detecting means further is adapted for generating a second response value associated with each response signal, based on a second characteristic of the response signals. Then, the second response values likewise are accumulated and sorted, into third and fourth sets of the values corresponding to the first and second pulses, respectively. The first processing means combines the second response values to generate third and fourth composite values. The second processing means compares the third and fourth composite values to generate a second difference factor that increases with the degree of difference between the third and fourth composite values. Finally, the third processing means selects one of the first and second difference factors for comparison to the threshold. Preferably the larger difference factor is selected. This is readily achieved by providing a fourth processing means operatively coupled to the second and third processing means, for comparing the difference factors, then causing the third processing means to select the larger difference factor for comparison with the threshold.

Once the selected characteristic is accepted, the control means can be employed to cause the pulse generator to produce incrementally varied tissue stimulation pulses, e.g. decremented from a level known to achieve capture. Evoked signals are sensed, and the eventual transition from the capture signature to the non-capture signature identifies the lowest tested energy level that exceeds the capture threshold. The energy level actually used should include the minimum plus a suitable safety margin.

In summary, a capture verification process is tested adaptively, taking into account changes that may occur over time, e.g. due to lead maturation, lead migration, myocardial substrate changes and any other factor effecting the stimulation threshold.

Thus in accordance with the present invention, one or more signal characteristics can be tested in situ to confirm their suitability as indicia of capture. The capability of confirming reliability, or alternatively discovering that a characteristic should not be relied upon, considerably increases the probability that subsequent self-testing and calibration more accurately pinpoint the capture threshold. This facilitates a more optimal selection and adjustment of tissue stimulation energy levels, to maintain effective pacing while extending the useful life of the pulse generator battery.

IN THE DRAWINGS

For a further understanding of the above and other features and advantages, reference is made to the following detailed description and to the drawings, in which.

DETAILED DESCRIPTION OF THE PREFERRED EMBODIMENTS

Figure 1:
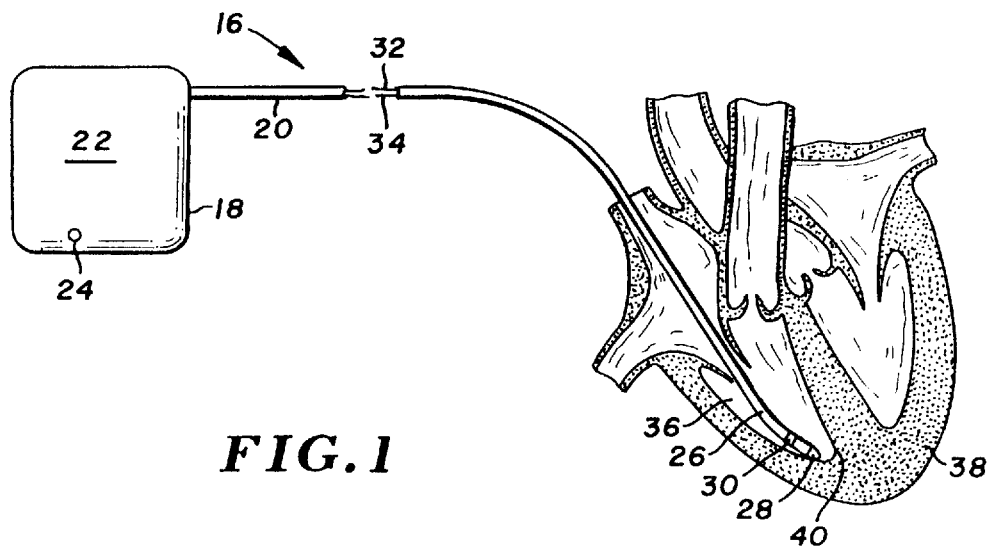
FIG. 1 is a diagrammatic view of a cardiac pacing system constructed in accordance with the present invention.

Turning now to the drawings, there is shown in FIG. 1 a cardiac pacing system 16, including a self-contained pacing and sensing unit 18 and an elongate catheter 20 electrically and mechanically coupled to unit 18. The pacing and sensing unit includes a hermetically sealed housing 22 formed of a biocompatible metal such as titanium, substantially covered by silicon rubber or other suitable insulative, biocompatible material. Housing 22 encloses logic circuitry used in generating tissue stimulating pulses and in sensing electrical activity in the tissue responsive to the pulses. A button electrode 24, typically in the form of an uncoated part of the housing, is coupled to circuitry inside the unit.

Catheter 20 is constructed of a flexible, dielectric material such as silicon rubber. At a distal end 26, catheter 20 supports a tip electrode 28 and a ring electrode 30. Electrodes 28 and 30 are electrically isolated from one another and spaced apart slightly, e.g. about 1 cm. Separate conductors 32 and 34, running the length of catheter 20, electrically couple the electrodes with circuitry inside the pacing and sensing unit. Conductors 32 and 34 are either individually insulated or contained within separate lumens formed in catheter 20, to electrically isolate them from one another.

In use, catheter 20 is inserted intravenously, e.g. into the subclavian vein or the cephalic vein, then progressively moved toward the heart until distal end 26 reaches a selected cardiac chamber. As illustrated in FIG. 1, the catheter is inserted to position distal tip electrode 28 and ring electrode 30 in the right ventricle 36 of the heart 38 near the apex 40. Pacing and sensing unit 18, implanted subcutaneously in the thoracic region, generates tissue stimulation pulses provided to tip electrode 28 via conductor 32. Tip electrode 28 thus is the drive electrode. With each pulse, a signal is transmitted to ring electrode 30 via tissue. Assuming an appropriately timed pulse with sufficient energy, this causes ventricular depolarization and contraction, i.e. achieves capture.

Conductor 32 and tip electrode 28 also are employed in sensing electrical activity in the myocardial tissue, in particular sensing for the presence or absence of a QRS complex (R wave) following a stimulation pulse. Conductor 30 and ring electrode 34 (acting as an indifferent electrode) also can form part of the sensing circuit, in which case system 16 senses signals in a bipolar mode. Alternatively, and as shown, button electrode 24 is employed as the indifferent electrode in a unipolar sensing mode. The unipolar mode provides response signals with more information, although they are more susceptible to noise from muscular motion and other artifacts. The sensing circuitry includes signal processing means, typically incorporating a sense amplifier for amplifying sensed voltages picked up by the electrodes, filtering circuitry for reducing noise falling outside of a selected range of frequencies, a rectifier circuit for producing an absolute valve of the amplified and filtered voltage and an integrator.

Figure 2:
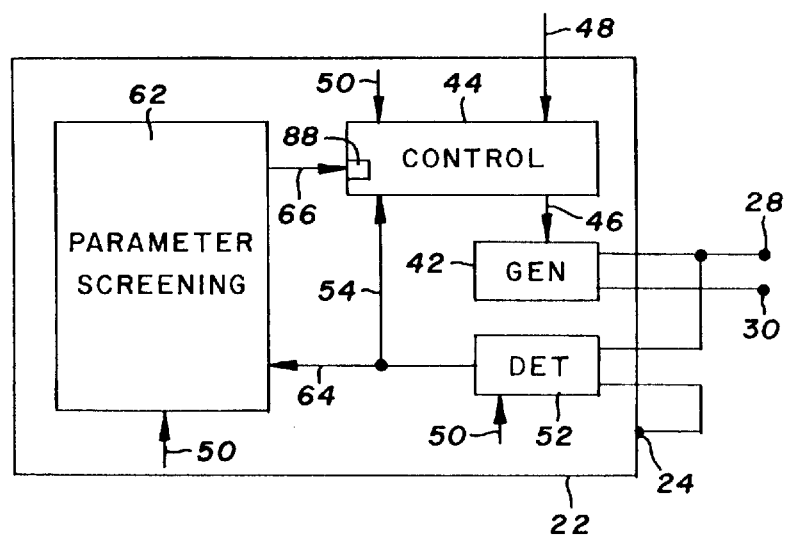
FIG. 2 is a block diagram of logic circuitry within a pacing and sensing unit of the system.

As seen in FIG. 2, logic circuitry inside housing 22 includes a pulse generating circuit 42 coupled to conductors 32 and 34, to supply the tissue stimulating pulses. A controller 44 incorporates logic circuitry programmable to govern the stimulating pulses as to amplitude, pulse width and frequency, through a controller output line 46 to the pulse generator circuit. The content of output line 46 depends on several inputs to the controller, including an external programming input 48 to select pulse characteristics and a clocking input 50.

A detector circuit 52 is coupled to tip electrode 28 and to button electrode 24, to sense electrical activity in tissue responsive to the stimulation pulses. The detector circuit provides response values to controller 44 via a line 54, to indicate the nature of the sensed activity, and thus indicate whether each tissue stimulation pulse evoked the desired response in myocardial tissue. Along with providing the response values, detector circuit 52 can notify the controller of the absence of a ventricular contraction over a predetermined time period and thereby cause the controller and generator circuit to provide a stimulating pulse.

Figure 3:
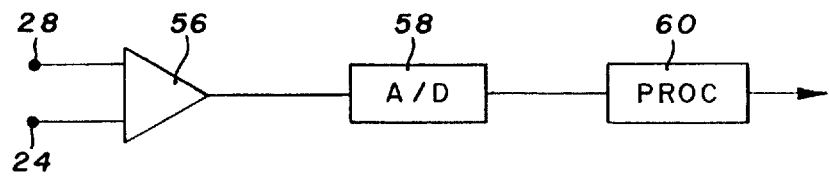
FIG. 3 is a schematic block diagram of signal detecting circuitry within the pacing and sensing unit.

As seen in FIG. 3, the detector circuit includes an amplifier 56 coupled to tip electrode 28, which functions as the active electrode while button electrode 24 functions as the indifferent electrode. The amplifier's analog output is provided to an analog-to-digital converter 58. The A/D converter in turn is coupled to provide its digital output to a digital processor 60, which generates the response values based on the digital information from the A/D converter. The response values can be based on absolute voltages, peak-to-peak voltages, values representing differentiations or integrations of the incoming signals, or other selected characteristics or parameters. The response values are provided to controller 44 in digital form, i.e. as binary words.

As previously noted, it is desired to provide pacing pulses at an energy level sufficient to ensure capture, yet not excessive as to unduly deplete a pacing unit battery (not shown). To this end, a self-test can be run, in which controller 44 governs generator circuit 42 to provide pulses of incrementally reduced amplitude until detector circuit 52 provides an output indicating non-capture. This determines the capture threshold, and controller 44 is programmed to set pacing pulses at a level greater than the threshold by a safety margin. This approach, however, depends in large part on (1) stability of the capture threshold, and (2) constancy of the evoked signals sensed by detecting circuit 52 in providing an unambiguous indication of capture versus non-capture. Neither of these is guaranteed, as capture thresholds and evoked signals vary from one patient to another, and vary with the same patient, over time.

The frequency of self-testing can be increased to compensate for a changing capture threshold. This does not address physical and other external factors that lead to changes in the evoked signals. Undetected, such changes can lead to false positive (indicating capture when there was none) or false negative messages from the detector circuit to the controller.

To address this problem, the logic circuitry within unit 18 incorporates a parameter screening circuit 62 which receives the response values as indicated at 64 and provides a screening output 66 to the controller. The screening circuit is digital and governed by clocking input 50.

Figure 4:
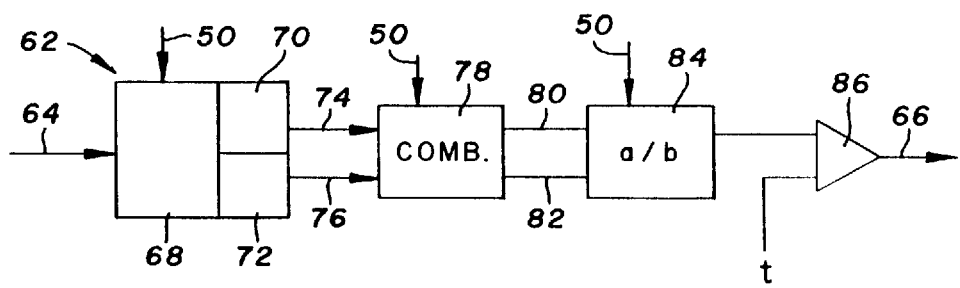
FIG. 4 is a schematic block diagram of logic circuitry within the unit for screening a test parameter.

As seen in FIG. 4, the screening circuit has several stages including a memory stage 68 for temporarily storing response values provided by the detection circuit. Memory stage 68, e.g. a read only memory (ROM), is adapted to accumulate multiple response values, preferably in the range of 50–100. Memory stage 68 also can distinguish among the response values, i.e. storing the response values in separate banks of registers 70 and 72 that for convenience can be considered as respective "capture" and "non-capture" banks of registers. Each of the response values is stored either in register bank 70 or in bank 72, depending on whether it is generated in response to a high energy pulse or a low energy pulse. In this context, a "high energy" pulse is one with sufficient amplitude and duration to ensure capture regardless of the tendency for capture thresholds to vary. A "low energy" pulse is discernible but known to be insufficient to cause capture, due to its low amplitude, narrow pulse width, or both. After multiple samples according to this distinction, register bank 70 contains a set of multiple response values in the form of binary words or bytes that reflect capture, while register bank 72 contains a set of multiple response values that reflect non-capture.

Lines 74 and 76 transmit the contents of banks 70 and 72 to a digital processing stage 78. At stage 78, the response values from register bank 70 are combined into a composite value "a", and the contents of register bank 72 are similarly combined into a composite value "b". For example, when the individual response values represent voltage levels, each composite value can indicate the average or mean voltage level based on the response values from the associated register bank. Thus each composite value a, b represents the response values in its associated set.

As indicated at 80 and 82, composite values a and b in the form of digital bytes or words, are provided to a processing stage 84 that generates an output a/b, the SNR representing the evoked responses due to capture, as compared to the responses in the absence of capture. At a final comparator stage 86, the value a/b is compared to a predetermined threshold "t". If the quantity a/b is either equal to or greater than the threshold, stage 86 generates an indication of acceptance, e.g. a binary "1". This indicates that the parameter or characteristic selected for measuring the evoked signals yields a ratio (SNR) selected for measuring the evoked signals yields a ratio (SNR) sufficiently large to clearly distinguish a response signal based on capture, from a response signal based on non-capture. If a/b is less than the threshold, stage 86 generates an indication of rejection, a binary "0".

Thus, circuit 62 screens a predetermined parameter or characteristic of signals generated in tissue responsive to pulses from generator circuit 42, to determine whether the parameter or characteristic provides a sufficient recognition differential to separate the capture and non-capture states. Output 66 from stage 86, the result of this screening, is provided to controller 44 as seen in FIG. 2. Responsive to an indication of acceptance, logic 88 in the controller enables a self-testing program. Pursuant to the program, stimulation pulses, initially at a sufficient amplitude and duration to ensure capture, are decreased until the measured parameter shifts from a range associated with capture, to a range associated with non-capture. For a parameter appropriately selected and screened as described, this shift tends to be abrupt and unambiguous. Accordingly the self-test determines the capture threshold and enables selection of an appropriate level (pulse amplitude and duration) for stimulation pulses to be used during normal operation of the pacing device.

Figure 5:
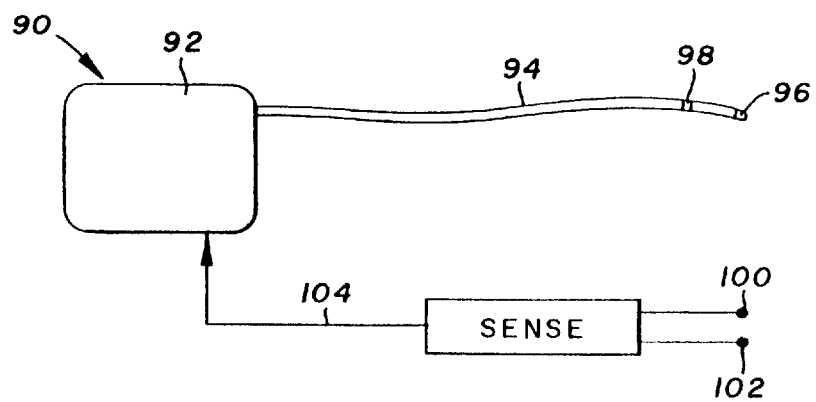
FIG. 5 is a diagrammatic view of an alternative embodiment cardiac pacing system.

FIG. 5 illustrates an alternative cardiac pacing and sensing system 90 in which the circuitry providing stimulation pulses and the circuitry that senses evoked responses are electrically independent. System 90 includes a pacing and sensing unit 92 and a catheter 94. The pulse generating circuitry includes tip and ring electrodes 96 and 98 at the distal end of the catheter, and respective conductors coupling the electrodes to pulse generating circuitry within the unit as previously described. The sensing circuit is shown schematically as a pair of sensing electrodes 100 and 102, coupled to provide a sensing input to unit 92 via a conductive line 104. In practice, the sensing circuit can take the form of an electrocardiogram (ECG) circuit with several surface electrodes, e.g. at the chest; an intracardiac electrocardiogram (EGM) circuit including at least one myocardial electrode; and a sensing catheter independent of catheter 94 and supporting several sensing electrodes. While a system with an independent sensing circuit is more expensive than the pacing and sensing system shown in FIG. 1, it affords an advantage of being less susceptible to post-shock effects in tissue, particularly near the electrodes.

As noted in connection with FIG. 4, parameter screening involves accumulating sets of response values associated with capture and with non-capture. To this end, the screening process includes generating multiple high energy and low energy pulses. Each response value must be clearly identified as to whether it occurred responsive to a high energy pulse or a low energy pulse. Clocking inputs 50 to controller 44, detector circuit 52 and memory stage 68 provide for the necessary identification. The clocking inputs further ensure that each individual pulse is temporally distinct from the others. It is advantageous to intersperse the low energy pulses among the high energy pulses, and more preferred to provide alternating high energy and low energy pulses. The preferred frequency of pulsing is determined by upper and lower limits. The upper limit is about 120 pulses per minute (ppm), due to physiologic considerations. Also, however, stimulation pulses should be generated at a frequency higher than the intrinsic heart rate. An example of a frequency within this preferred range is 100 ppm.

Figure 6:
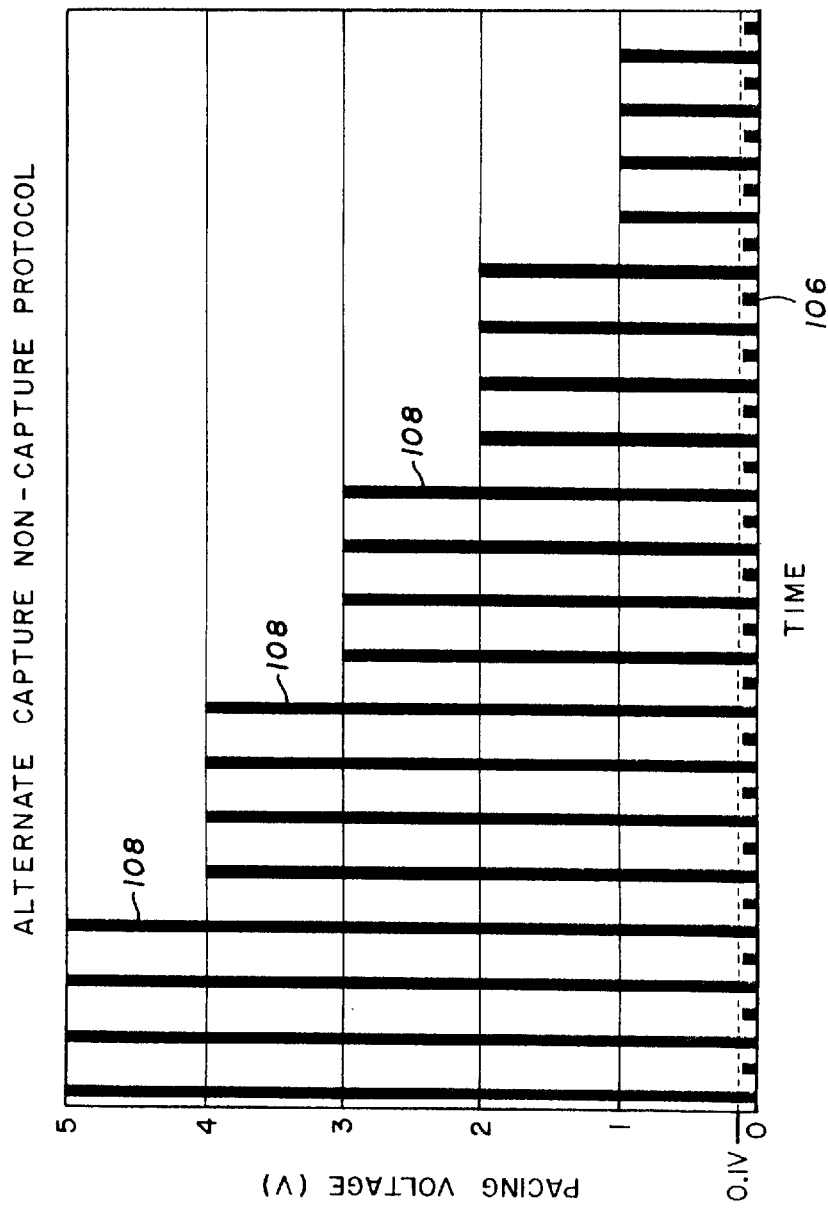
FIG. 6 is a chart showing a pulse delivery protocol for using the pacing system to screen a test parameter.

The chart in FIG. 6 shows one particularly preferred stimulation protocol. According to the protocol, a plurality of low energy pulses 106 are interspersed among a plurality of high energy pulses 108. The pulses are generated in a sequence of alternating high energy and low energy pulses, at an overall frequency or pulse rate of 100 ppm.

High energy pulses 108 are decremented in stepped fashion. More particularly, the first four high energy pulses are generated at an amplitude of 5 volts, the next four pulses 108 are provided at 4 volts, etc. Also, however, decrementing the amplitude is not continued to a point sufficiently near the expected capture threshold such that "high energy" pulses risk failure to achieve capture. It should be recognized that the pattern of high energy pulses shown (groups of four, one volt decrement) is but one of many suitable patterns. Depending on the patient, it may be appropriate to change the number of high energy pulses in each group, change the amount of the voltage decrement, or even to provide a change in voltage that gradually increases or diminishes as the protocol proceeds. While FIG. 6 illustrates 40 pulses as a matter of convenience, a range of 50–100 pulses is recommended.

Figure 7:
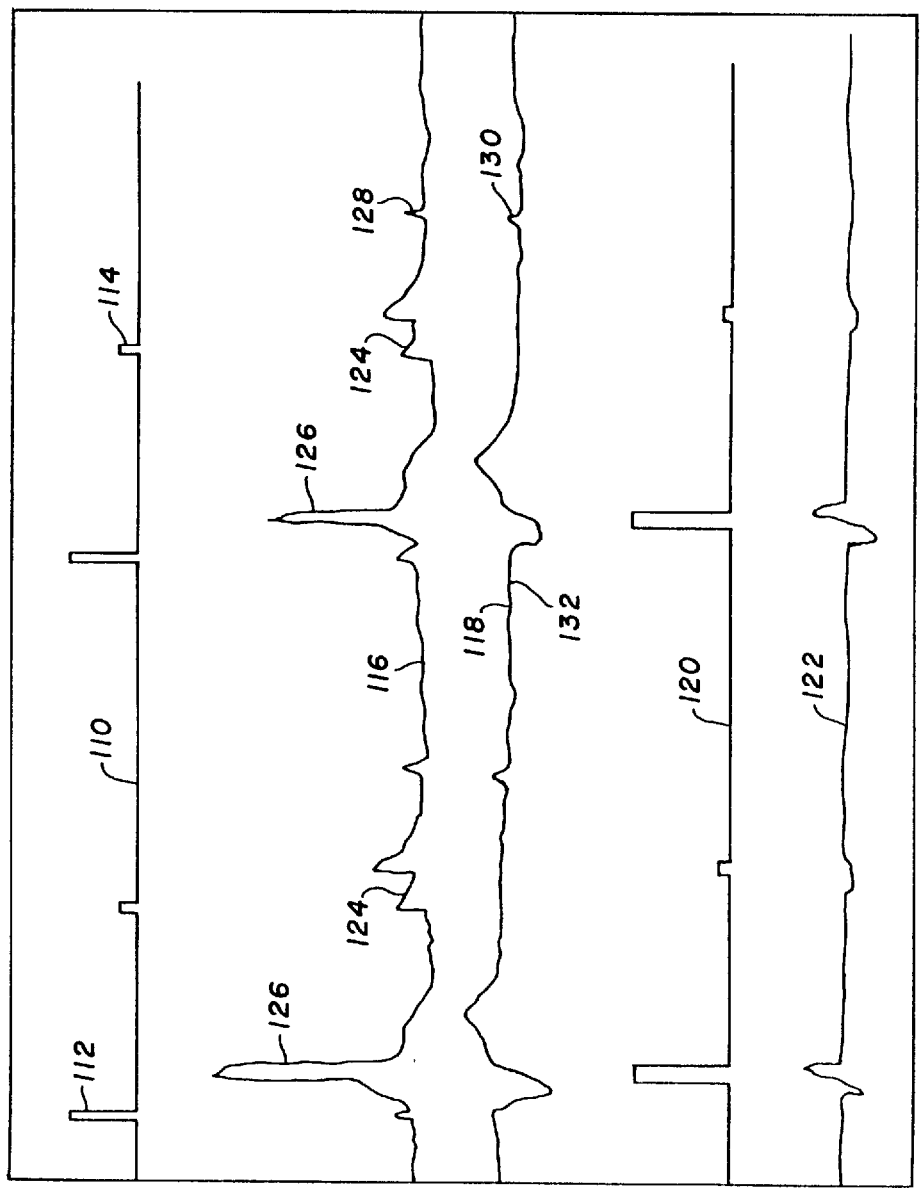
FIG. 7 is a timing diagram showing a sequence of pulses delivered according to the protocol and resulting sensed signals.

FIG. 7 is a timing diagram illustrating tissue stimulation pulses provided under the alternating capture/non-capture protocol, and several resulting signals. The timing diagram relates to a portion of the protocol illustrated in FIG. 6, i.e. where the high energy pulses have an amplitude of 2.0 volts and a duration of 0.5 ms. Line 110 indicates alternating high energy and low energy stimulation pulses, indicated at 112 and 114, respectively. Line 116 represents evoked signals in the myocardial tissue, as sensed by an intracardiac electrogram (EGM). Line 118 detects the same evoked signals, as sensed by an electrocardiogram (ECG). Line 122 is a windowed EGM that represents the signals passed into the parameter evaluation process and contains only the time periods appropriate period for evoked responses. Line 120 shows the parameter value output, and has one value for each pace pulse.

With reference to line 110, the low energy pulses need not occur exactly midway between the preceding and succeeding high energy pulse, but should follow the preceding high energy pulse by at least 545 ms as shown, to account for the refractory period. As seen along line 116, the 2 volt pulses leave some residual energy 124 at the point of generating the low energy pulse, 545 ms after the high energy pulse. This energy level is sensed as the "noise" associated with non-capture and is compared to the signals 126 following the high energy pulses. The ECG (line 118) registers capture, but does not reflect the residual energy sensed by the EGM. Spikes at 128 and 130 indicate a sinus beat. A flat base line after a sinus beat, indicated at 132, indicates the absence of residual energy. i.e. the inclined base line after each high energy pulse 112. The alternating capture/non-capture sequence may be interrupted by normal sinus activity and continue without restarting when sinus activity is absent.

Figure 8:
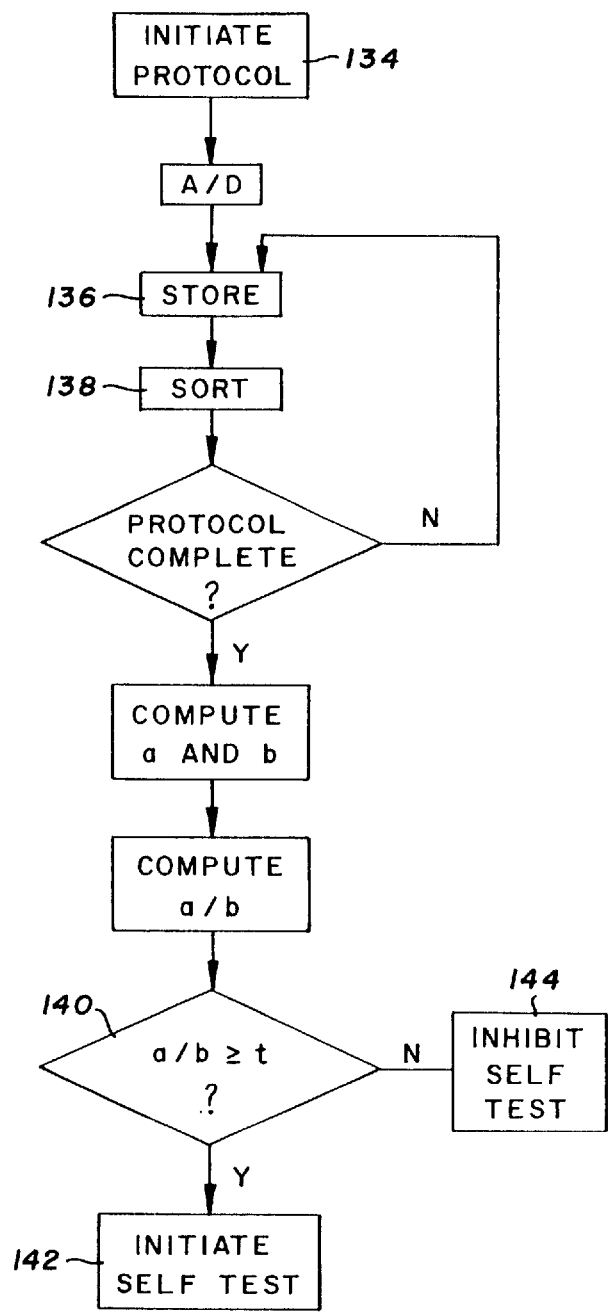
FIG. 8 is a flow chart illustrating a sequence of steps in screening a test parameter.

Parameter screening proceeds according to the flow chart of FIG. 8. The protocol is initiated at 134, with an evoked response in tissue sensed after each generated pulse. Each sensed signal is digitized and processed, with the resultant response value provided to memory stage 58. A storing function 136 and a sorting function 138, although shown separately, can be performed simultaneously. Successive response values, tied to the appropriate pulses by clocking signals 50, are thus identified as to storage destination and stored in the appropriate one of register banks 70 and 72.

Completion of the protocol can be determined in a manner known in the art, for example by accumulating a count of response values as they are stored, or based on the clocking input in view of the predetermined pulse frequency. Completion of the protocol enables computation at stage 78 of composite values a and b. Most preferably, these are the average or mean response values for capture and non-capture, respectively. Further computations can be performed at this stage, e.g. standard deviations for the respective sets of capture/non-capture response values. Then stage 84 computes the ratio of a to b.

Next, the a/b ratio is compared to threshold value t at 140. If the ratio exceeds the threshold, a self-testing procedure is initiated at 142, since the screening procedure has confirmed that the predetermined parameter exhibits a sufficient recognition differential to separately identify the capture and non-capture states.

Self-testing then proceeds in a known manner, e.g. by providing an initial signal guaranteed to evoke capture, then decrementing the signal until the non-capture response is identified, thereby to at least approximately determine the capture threshold.

Alternatively, if the ratio a/b is found to be less than the threshold, the self-test is inhibited, as indicated at 144.

Figure 9:
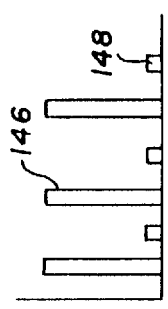
FIGS. 9 and 10 illustrate alternative pulse delivery protocols for parameter testing.
Figure 10:
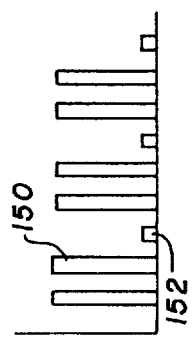

FIGS. 9 and 10 are charts illustrating two alternative parameter screening protocols. In FIG. 9, high energy pulses 146 are provided at a constant amplitude and pulse width, e.g. 3 volts and 0.5 ms, respectively. Low energy pulses 148 are generated at constant amplitude and pulse width values of 0.1 volt and 0.05 ms, respectively. Pulses 146 and 148 are provided in alternating order and at a frequency of 100 ppm, so that the only difference from the protocol shown in FIG. 5 is the lack of decrementing the high energy pulses.

In FIG. 10, high energy pulses 150 and low energy pulses 152 are again provided at constant amplitudes and pulse widths. Low energy pulses 152 are interspersed among the high energy pulses. Rather than alternating, the pattern is such that every third pulse is a low energy pulse. The opposite of this pattern (every third pulse being high energy) is not recommended, due to an excessive time span between adjacent high energy pulses.

Figure 11:
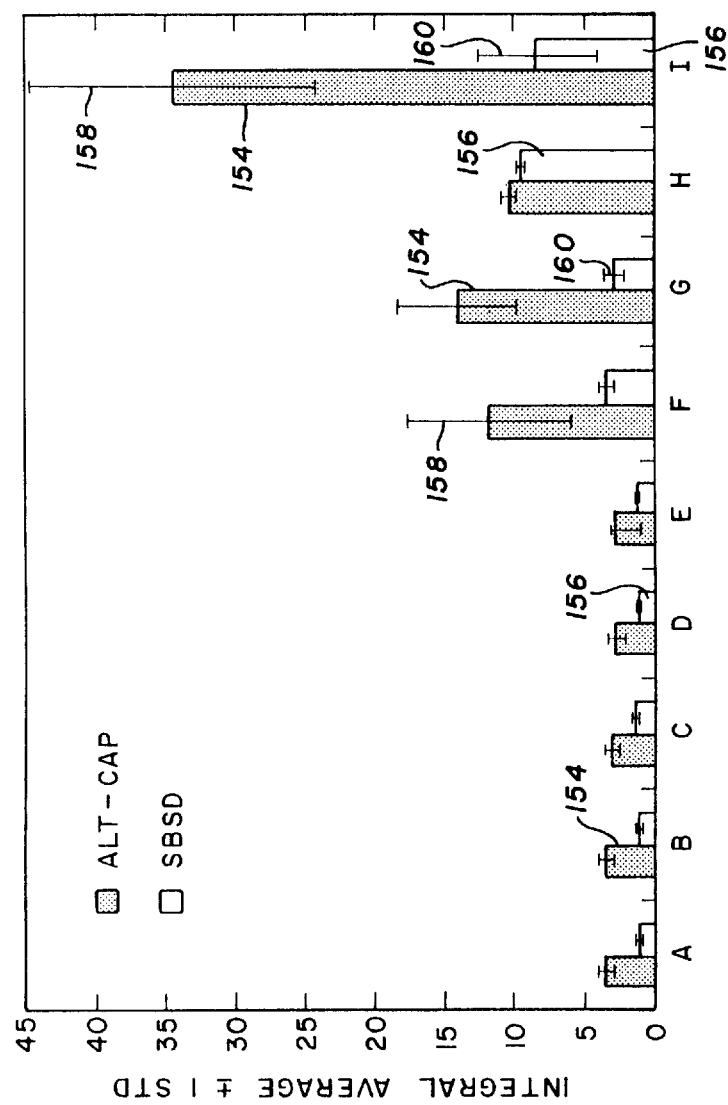
FIGS. 11 and 12 are charts comparing the protocol of FIG. 6 and a single beat step-down (SBSD) protocol with respect to integrated averages and signal-to-noise ratios.
Figure 12:
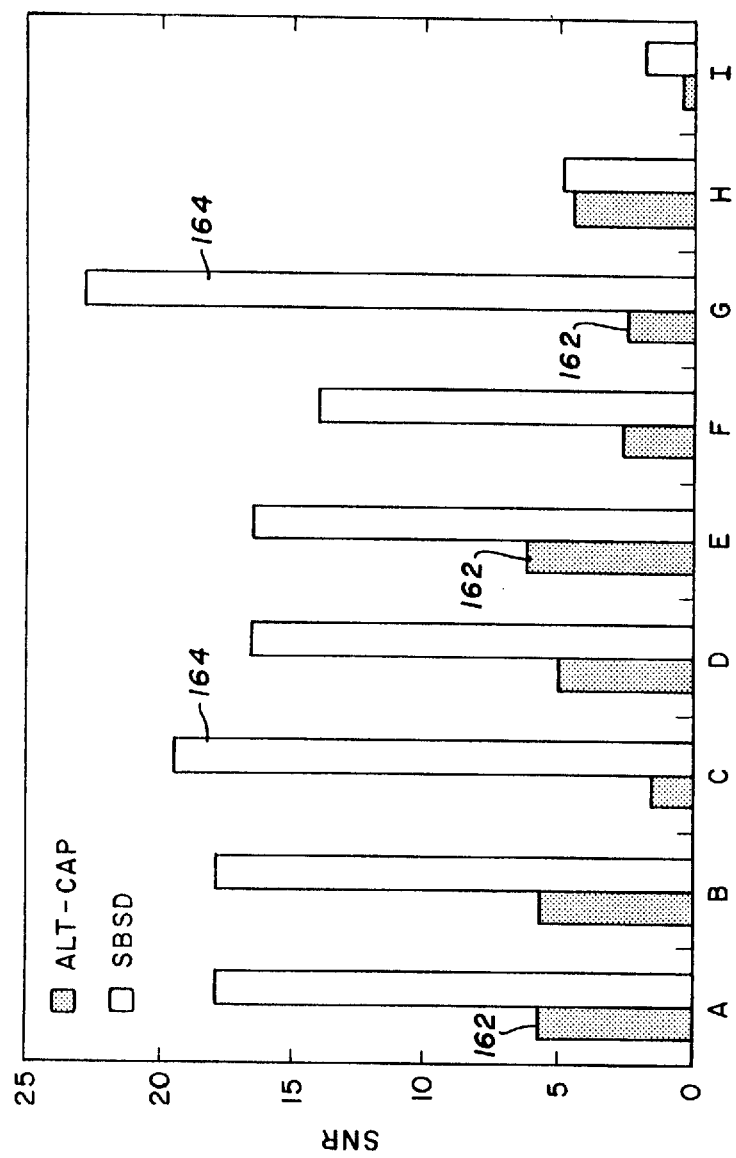

The protocol of FIG. 6 has several advantages. The first is the generation of alternating high and low energy pulses. The alternating sequence provides a "worst case" environment for screening, in the sense that the non-capture response values tend to be higher than they would be under different protocols. This is perhaps best understood from FIGS. 11 and 12 illustrating comparative integral averages and signal-to-noise ratios, respectively, for nine different patients. In particular, the chart of FIG. 11 includes nine sets of side-by-side vertical bars 154 and 156. Each vertical bar 154 represents the integral average of multiple non-capture response signals, obtained according to the alternating capture/non-capture protocol. Vertical bars 156 also indicate integral averages based on non-capture response values, but under a single beat step down (SBSD) protocol. In the SBSD protocol, stimulus intensity is monotonically decreased from a known capture level, e.g. 5 volts, to a non-capture level. The top of each bar is the mean or average, i.e. the composite value. Also shown with the bars are respective vertical lines 158 and 160, indicating the range of plus and minus one standard deviation.

In each case, the composite value based on the alternating capture/non-capture protocol exceeds the counterpart composite value based on SBSD, although the degree of difference varies. Standard deviations, likewise, are greater in the case of alternating capture/non-capture.

FIG. 12 is a chart with side-by-side vertical bars 162 and 164 indicating signal-to-noise ratios produced under the alternating capture/non-capture protocol and the SBSD protocol, respectively. In each case, the alternating capture/non-capture protocol yields a lower SNR, although the degree of difference varies. Accordingly, the alternating capture/non-capture protocol provides a more rigorous screening of the chosen parameter. The resulting ratio of the "capture" composite value to the "non-capture" composite value is lower, i.e. more likely to be closer to a predetermined acceptance threshold. Thus the alternating capture/non-capture protocol is less likely to accept a marginal parameter for self-testing. This protocol similary is preferred over other protocols, e.g. eight beat step down, and repeated singlebeat closed loop auto-detect.

A further advantage of the protocol in FIG. 6, as compared to those in FIGS. 9 and 10, is the decrementing of the high energy pulses. When the high energy pulses are decremented, albeit maintained above the capture threshold, they cause storage of information to register bank 70 that takes into account any variance in the sensed capture signal due to the different pulsing amplitudes. Thus, the resulting composite value "a" takes this information into account.

Figure 13:
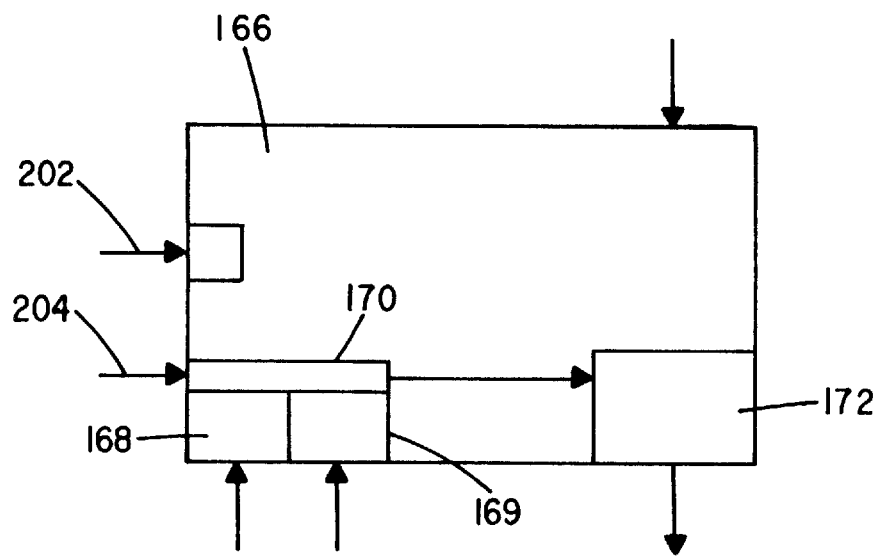
FIGS. 13–15 are schematic block diagrams showing logic circuitry for screening more than one parameter in another alternative embodiment pacing system.
Figure 14:
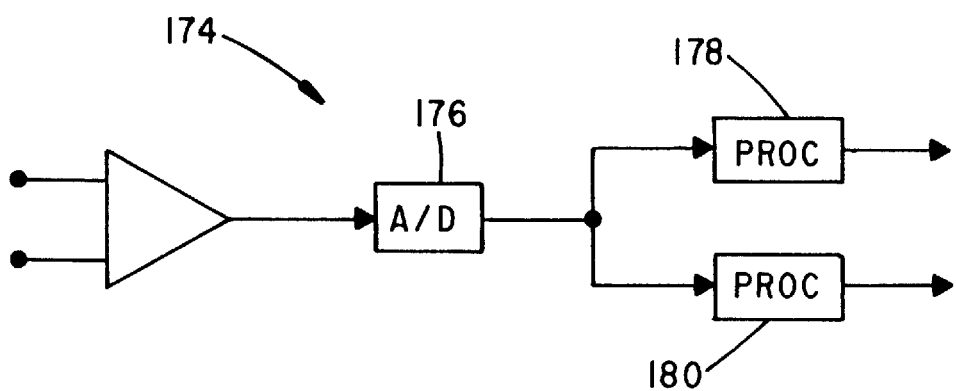
Figure 15:
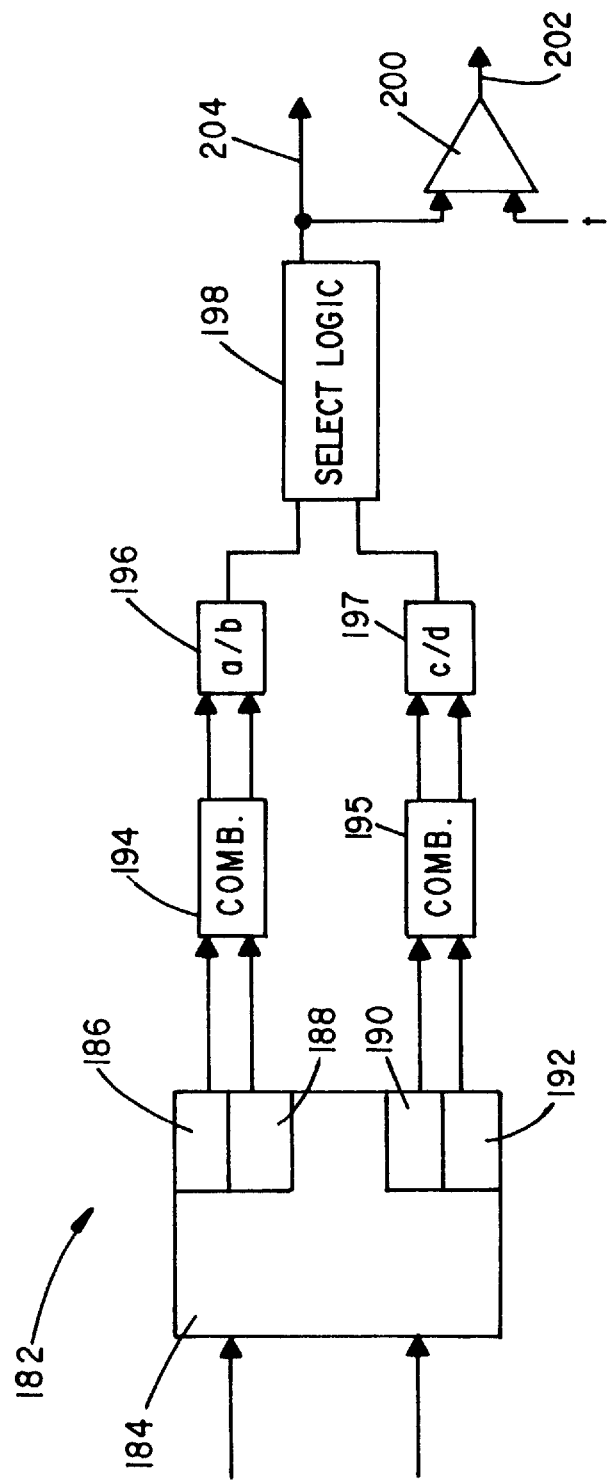

FIGS. 13–15 illustrate portions of an alternative pacing and sensing system in which several predetermined parameters can be simultaneously screened for use in self-testing. The alternative system includes a pacing and sensing unit and catheter, much like those in system 16 in FIG. 1. The alternative unit incorporates similar components of logic circuitry, including a controller, pulse generator circuit, detector circuit and screening circuit as shown in FIG. 2. As shown in FIG. 13, a controller 166 of the alternative system incorporates circuits 168 and 169 for receiving two inputs from the detector circuit, representing response values based on two different signal characteristics. As an example, one set of the response values can be based on an integration of the sensed signal, and the other set can represent a peak-to-peak amplitude difference. A select logic circuit 170 provides one of the response values as in input to a drive logic circuit 172 of the controller.

FIG. 14 illustrates a detector 174 of the alternative system, which is similar to detector circuit 52 except that an A/D converter 176 provides its output to two processors 178 and 180 that generate the two different response values. These response values are provided to circuits 168 and 169 of the controller, and to a screening circuit 182. As seen in FIG. 15, the screening circuit has major components similar to those of circuit 62 in FIG. 4, but with added features to accommodate the added response values. A memory 184 receives the two response values as inputs and stores the capture and non-capture instances of the first response value in respective first and second register banks 186 and 188. Further, the memory incorporates third and fourth register banks 190 and 192 for storing capture and non-capture instances of the second response values. Four accumulations of data are provided by the memory to processing stages 194 and 195, for computation of composite values a, b, c and d, each based on data from its associated one of the register banks.

The resultant outputs a–d are provided to a further processing stage 196, which generates two outputs: the ratio a/b comparing capture and non-capture values of the first parameter; and the ratio c/d, the comparison of the capture and non-capture values for the second parameter. These ratios are provided to a selection logic circuit 198, which generates the larger ratio as its output. Thus, it is only the selected ratio that is compared to the predetermined threshold t at a comparator stage 200. As before, this stage generates an indication of acceptance or rejection, e.g. either a binary 1 or a binary 0. The screening indication, designated 202, also is shown in FIG. 13 as an input to self-test logic 203 in the controller.

The selected ratio a/b (or alternatively, c/d) also is provided from selection logic 198 to the controller, as indicated at 204. Again with reference to FIG. 13, this ratio is provided as an input to selection logic 170 in the controller, and governs which of receiving circuits 168 and 169 is operatively associated with the drive logic to control pulse generation.

While FIGS. 13–15 depict the screening of two signal parameters or characteristics, it is readily appreciated that three or more parameters can be simultaneously screened in the same manner, by adding the appropriate number of processors in the detector circuit, register banks and associated circuitry in screening circuit, and receiving circuits in the controller.

Thus in accordance with the present invention, a chosen signal characteristic or parameter can be screened prior to self-testing a pacing device, to ensure that the selected parameter can reliably distinguish capture from non-capture. Reliability in this regard is enhanced by the accumulation of multiple response values reflecting capture and non-capture, and processing the information of these multiple episodes into cumulative values or signatures of capture and non-capture, respectively. Evoked signals can be sensed with respect to two or more characteristics, with information processing including a comparison step to determine which of the characteristics is likely to be the most reliable. Finally in accordance with the present invention, an implanted pacing and sensing system can be periodically adjusted, not only to re-evaluate thresholds based on a given parameter, but also to screen the given parameter itself, and if appropriate to select an alternative parameter as a more reliable basis for assessing the threshold. The system is self-adaptive, choosing the most suitable parameter in response to changing biodynamics of the myocardium and pacing lead.

What is claimed is:

1. A process for testing the efficacy of a sensed parameter as an indication of tissue stimulation; including:
  applying a plurality of first pulses to tissue, each of the first pulses having at least a first level of intensity known to evoke a desired response in the tissue;
  applying a plurality of second pulses to the tissue in a manner to intersperse said second pulses within the plurality of first pulses, each of the second pulses having at most a second level of intensity known to be insufficient to evoke said desired response, with each of the pulses temporally distinguishable from the other pulses;
  after applying each of the pulses, sensing the tissue to generate a response value based on a selected parameter, each one of the response values corresponding to one of said first and second pulses;
  accumulating and sorting the response values into a first set of the response values corresponding to the first pulses and a second set of the response values corresponding to the second pulses;
  combining the response values of said first set into a first composite value, and combining the values of said second set into a second composite value;
  comparing the first composite value and the second composite value to one another to produce a difference factor based on the comparison; and
  comparing the difference factor to a predetermined threshold, and alternatively:
    (i) indicating an acceptance of the selected parameter responsive to determining that the difference factor is at least equal to the threshold; and
    (ii) indicating a rejection of the parameter responsive to determining that the difference factor is less than the threshold.

2. The process of claim 1 wherein:
  said sensing of the tissue comprises sensing voltage, and each of said response values represents a voltage level.

3. The process of claim 1 wherein:
  said sensing of the tissue includes detecting voltage, and each of the response values represents a peak-to-peak amplitude of a signal.

4. The process of claim 1 wherein:
  said sensing of tissue to accumulate said response values includes differentiating the sensed signals.

5. The process of claim 1 wherein:

said sensing of the tissue includes sensing voltages, filtering the voltages to a selected range of frequencies, rectifying the signals and integrating the signals over a specified time.

6. The process of claim 1 wherein:

said combining of the first and second response values to generate respective first and second composite values includes generating respective first and second averages of the first and second signals.

7. The process of claim 1 wherein:

said combining of the response values includes determining respective first and second integrated averages and first and second standard deviations corresponding respectively to the first and second sets of response values.

8. The process of claim 1 further including:

in the event of indicating acceptance of the selected parameter, applying test pulses of incrementally varied intensity levels to the tissue while sensing the tissue, to determine a minimum of said intensity levels at which the test pulses evoke the desired response.

9. The process of claim 8 wherein:

applying the test pulses includes applying the pulses initially at an upper level known to evoke the desired response, then decrementing the level toward said second level of intensity.

10. The process of claim 8 wherein:

said applying includes applying the test pulses initially at a lower level of intensity known to be insufficient to evoke a desired response, then incrementally increasing the level toward said first level.

11. The process of claim 1 wherein:

said tissue is cardiac tissue, and the desired response is a capture.

12. The process of claim 11 wherein:

said second pulses are interspersed among the first pulses in a manner to prevent an occurrence of two or more consecutive second pulses.

13. The process of claim 12 wherein:

said first and second pulses are interspersed in a manner to provide alternating first and second pulses.

14. The process of claim 13 wherein:

said pulses are provided at a frequency that exceeds an intrinsic heart rate.

15. The process of claim 14 wherein:

said first pulses are applied initially at a selected maximum level of intensity substantially higher than said first level, then progressively decremented toward said first level.

16. The process of claim 1 wherein:

said first and second levels of intensity are determined by a combination of pulse amplitude and pulse duration, with said first level of intensity being an amplitude of at least one volt and a duration of at least 0.5 ms; and said second level of intensity is an amplitude of at most about 0.1 volt and a duration of at most about 0.05 ms.

17. A system for automatically determining the efficacy of a detected response in tissue as an indication of tissue stimulation including:

a pulse generator;

a conductive pulse transmitting means coupled between the pulse generator and tissue, for delivering pulses to the tissue;

a control means operatively coupled to the pulse generator for selectively varying an intensity level of the pulses, and thereby causing the pulse generator to deliver the pulses according to a protocol in which: (i) a plurality of first pulses having at least a first level of intensity known to achieve a desired response are interspersed among a plurality of second pulses having at most a second level of intensity known to be insufficient to achieve the desired response; and (ii) each of the pulses is temporally distinct from the others;

a detecting means for sensing a response signal in said tissue following each of the first and second pulses, and adapted for generating at least a first response value associated with each response signal, based on a first characteristic of the response signals;

a storage means adapted for accumulating the response values;

a sorting means adapted for sorting the accumulated response values into a first set corresponding to the first pulses and a second set corresponding to the second pulses;

a first processing means for combining the response values to generate first and second composite values based on the first and second sets, respectively;

a second processing means operatively coupled to the first processing means, for comparing the first and second composite values and generating a difference factor based on the degree of difference between the first and second composite values;

a third processing means coupled to receive the output of the second processing means, adapted for comparing the difference factor to a threshold, and for providing, either:

(i) an indication of acceptance of the characteristic responsive to determining that the difference factor is at least as great as the threshold; or (ii) an indication of rejection of the characteristic responsive to determining that the difference factor is less than the threshold.

18. The system of claim 17 wherein:

said first characteristic of the associated response signal comprises one of the following: a voltage level of the signal, and a peak-to-peak amplitude of the signal.

19. The system of claim 17 wherein:

said first composite value and said second composite value comprise integrated averages of the response values in said first and second sets, respectively.

20. The device of claim 19 wherein:

said first processing means further generates respective first and second standard deviations based on the response values in the first and second sets, respectively.

21. The device of claim 17 wherein:

said detecting means further is adapted for generating a second response value associated with each response signal based on a second characteristic of the response signals;

the storage means further is adapted to accumulate said second response values, and said sorting means further is adapted to sort the accumulated second response values into a third set corresponding to the first pulses and a fourth set corresponding to the second pulses;

the first processing means further is adapted to combine the second response values to generate third and fourth composite values based on the third and fourth sets, respectively;

the second processing means further is adapted to compare the third and fourth composite values and generate a second difference factor based on the degree of difference between the third and fourth composite values; and said third processing means further is adapted to select one of said first and second difference factors for the comparison to said threshold, to determine whether the selected difference factor is at least as great as the threshold.

22. The device of claim 21 further including:

a fourth processing means operatively coupled to the second and third processing means, for comparing the first and second difference factors, and for selecting the larger of the first and second difference factors, thereby to cause said third processing means to select said larger difference factor for the comparison to said threshold.

23. The device of claim 17 further including:

means, responsive to said indication of acceptance, for applying test pulses of incrementally varied intensity levels to the tissue while measuring said first characteristic, to determine a minimum intensity level at which the test pulses evoke the desired response.

24. The device of claim 23 wherein:

said means is adapted to provide test signals initially at an upper level of intensity known to evoke the desired response, then to decrement the signals toward said second level of intensity.

25. The device of claim 17 wherein:

said control means comprises programmable logic circuitry.

26. The device of claim 25 wherein:

said logic circuitry is programmed to provide the second pulses interposed among the first pulses in a manner to prevent the occurrence of more than one consecutive second pulse.

27. The device of claim 26 wherein:

said logic circuitry is programmed to provide the first and second pulses in an alternating sequence.

28. The device of claim 17 wherein:

said detecting means includes a plurality of sensing electrodes, an A/D conversion circuit in the pulse generator, and an electrically conductive pathway between the sensing electrodes and the A/D conversion circuit, whereby said response values are binary words representing voltage levels sensed by the sensing electrodes.

29. The device of claim 17 wherein:

said second processing means incorporates circuitry for dividing the first composite value by the second composite value, whereby the difference factor is a ratio of the first and second composite values.

30. The device of claim 17 wherein:

said storage means comprises a first bank of registers for storing the accumulated response values of said first set, and a second bank of registers for storing the accumulated response values of said second set; and said sorting means includes clocking signals for simultaneously governing the operation of the pulse generator and memory circuitry including the first and second banks of registers, for determining in connection with each sensed response signal the associated one of the first and second pulses and, responsive thereto, loading the response value to the associated one of the first and second banks of registers.

31. A process for comparatively determining the efficacy of two or more sensed parameters as indications of tissue stimulation; including:

applying a plurality of first pulses to tissue, each of the first pulses having at least a first level of intensity known to evoke a desired response in the tissue;

applying a plurality of second pulses to the tissue in a manner to intersperse the second pulses within the plurality of first pulses, each of the second pulses having at most a second level of intensity known to be insufficient to evoke the desired response, and wherein each of the pulses is temporally distinguishable from the other pulses;

sensing the tissue for an evoked signal after applying each of the pulses, and using each evoked signal to generate a first response value based on a first selected parameter and a second response value based on a second selected parameter of the evoked signals, whereby each of the first response values and each of the second response values corresponds to one of the first and second pulses;

accumulating the response values and sorting the response values into: (i) a first set including the first response values corresponding to the first pulse; (ii) a second set including the first response values corresponding to the second pulse; (iii) a third set including the second response values corresponding to the first pulse; and (iv) a fourth set including the second response values corresponding to the second set;

combining the response values of these sets respectively into first, second, third and fourth composite values;

comparing the first composite value and the second composite value to one another to produce a first difference factor based on the comparison, and comparing the third and fourth composite values to one another to produce a second difference factor based on the comparison; and selecting one of the difference factors, thereby to select the parameter associated with the selected difference factor.

32. The process of claim 31 wherein:

the step of selecting one of the difference factors includes selecting the larger of the first and second difference factors.

33. The process of claim 31 further including:

comparing the selected difference factor to a predetermined threshold, and alternatively:

(i) indicating an acceptance of the associated parameter responsive to determining that the selected difference factor is at least equal to the threshold; or (ii) indicating a rejection of the associated parameter responsive to determining that the selected difference factor is less than the threshold.

34. The process of claim 31 wherein generating the response values includes measuring each of the evoked signals for (i) a voltage level to obtain the first response value, and (ii) a peak-to-peak amplitude to provide the second response value.

* * * * *

UNITED STATES PATENT AND TRADEMARK OFFICE
CERTIFICATE OF CORRECTION

PATENT NO. : 5,855,594
DATED : January 5, 1999
INVENTOR(S) : Arthur L. Olive, et al.

It is certified that error appears in the above-indentified patent and that said Letters Patent is hereby corrected as shown below:

Claim 35, (column 6) (line 52) change "alternatively" to -- either --.

Signed and Sealed this

Twenty-fifth Day of May, 1999

Q. TODD DICKINSON

Attest:

Attesting Officer

Acting Commissioner of Patents and Trademarks